(12) United States Patent
Yang et al.

(10) Patent No.: US 7,557,124 B2
(45) Date of Patent: Jul. 7, 2009

(54) TETRAHYDROPYRANYL CYCLOPENTYL TETRAHYDROPYRIDOPYRIDINE MODULATORS OF CHEMOKINE RECEPTOR ACTIVITY

(75) Inventors: Lihu Yang, Edison, NJ (US); Sander G. Mills, Scotch Plains, NJ (US); Richard Jiao, Havertown, PA (US)

(73) Assignee: Merck & Co., Inc., Rahway, NJ (US)

( * ) Notice: Subject to any disclaimer, the term of this patent is extended or adjusted under 35 U.S.C. 154(b) by 260 days.

(21) Appl. No.: 11/587,288

(22) PCT Filed: Apr. 22, 2005

(86) PCT No.: PCT/US2005/013754

§ 371 (c)(1),
(2), (4) Date: Oct. 23, 2006

(87) PCT Pub. No.: WO2005/120505

PCT Pub. Date: Dec. 22, 2005

(65) Prior Publication Data

US 2008/0021061 A1 Jan. 24, 2008

Related U.S. Application Data

(60) Provisional application No. 60/565,380, filed on Apr. 26, 2004.

(51) Int. Cl.
*C07D 405/02* (2006.01)
*C07D 309/14* (2006.01)
*A61K 31/47* (2006.01)
*A61K 31/351* (2006.01)

(52) U.S. Cl. .................. 514/307; 514/459; 546/146; 549/424

(58) Field of Classification Search .................. None
See application file for complete search history.

(56) References Cited

U.S. PATENT DOCUMENTS

2002/0049222 A1 4/2002 Yang et al.

FOREIGN PATENT DOCUMENTS

WO WO 03/092586 A2 11/2003

*Primary Examiner*—Zinna N Davis
(74) *Attorney, Agent, or Firm*—James L. McGinnis; Mark R. Daniel

(57) ABSTRACT

Compounds of Formula I:

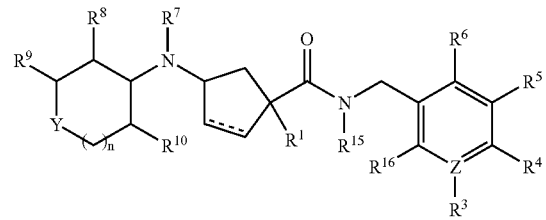

(wherein n, $R^1$, $R^3$, $R^4$, $R^5$, $R^6$, $R^7$, $R^8$, $R^9$, $R^{10}$, $R^{15}$, $R^{16}$, Y and Z are as defined herein) which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

13 Claims, No Drawings

US 7,557,124 B2

TETRAHYDROPYRANYL CYCLOPENTYL TETRAHYDROPYRIDOPYRIDINE MODULATORS OF CHEMOKINE RECEPTOR ACTIVITY

RELATED APPLICATION DATA

This is a National filing under 35 USC 371 of PCT/US2005/013754, filed Apr. 22, 2005, which claims priority from U.S. Ser. No. 60/565,380, filed Apr. 26, 2004.

BACKGROUND OF THE INVENTION

The chemokines are a family of small (70-120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, *Cytokine*, 3, 165-183 (1991) and Murphy, *Rev. Immun.*, 12, 593-633 (1994)). These molecules were originally defined by four conserved cysteines and divided into two subfamilies based on the arrangement of the first cysteine pair. In the CXC-chemokine family, which includes IL-8, GROα, NAP-2 and IP-10, these two cysteines are separated by a single amino acid, while in the CC-chemokine family, which includes RANTES, MCP-1, MCP-2, MCP-3, MIP-1α, MIP-1β and eotaxin, these two residues are adjacent.

The □-chemokines, such as interleukin-8 (IL-8), neutrophil-activating protein-2 (NAP-2) and melanoma growth stimulatory activity protein (MGSA) are chemotactic primarily for neutrophils, whereas □-chemokines, such as RANTES, MIP-1□, MIP-1□, monocyte chemotactic protein-1 (MCP-1), MCP-2, MCP-3 and eotaxin are chemotactic for macrophages, monocytes, T-cells, eosinophils and basophils (Deng, et al., *Nature*, 381, 661-666 (1996)).

The chemokines are secreted by a wide variety of cell types and bind to specific G-protein coupled receptors (GPCRs) (reviewed in Horuk, *Trends Pharm. Sci.*, 15, 159-165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.*, 270, 22123-22128 (1995); Beote, et al, *Cell*, 72, 415-425 (1993)); CCR-2A and CCR-2B (or "CKR-2A"/"CKR-2A" or "CC-CKR-2A"/"CC-CKR-2A") [MCP-1, MCP-2, MCP-3, MCP-4]; CCR-3 (or "CKR-3" or "CC-CKR-3") [Eotaxin, Eotaxin 2, RANTES, MCP-2, MCP-3] (Rollins, et al., *Blood*, 90, 908-928 (1997)); CCR-4 (or "CKR-4" or "CC-CKR-4") [MIP-1α, RANTES, MCP-1] (Rollins, et al., *Blood*, 90, 908-928 (1997)); CCR-5 (or "CKR-5" or "CC-CKR-5") [MIP-1α RANTES, MIP-1β] (Sanson, et al., *Biochemistry*, 35, 3362-3367 (1996)); and the Duffy blood-group antigen [RANTES, MCP-1] (Chaudhun, et al., *J. Biol. Chem.*, 269, 7835-7838 (1994)). The β-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., *Arthritis & Rheumatism*, 42, 989-992 (1999)). A review of the role of eosinophils in allergic inflammation is provided by Kita, H., et al., *J. Exp. Med.* 183, 2421-2426 (1996). A general review of the role of chemokines in allergic inflammation is provided by Lustger, A. D., *New England J. Med.*, 338(7), 426-445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and *Listeria monocytogenes* infection (Lu et al., *J. Exp. Med.*, 187, 601-608 (1998); Kurihara et al. *J. Exp. Med.*, 186, 1757-1762 (1997); Boring et al. *J. Clin. Invest.*, 100, 2552-2561 (1997); Kuziel et al. *Proc. Natl. Acad. Sci.*, 94, 12053-12058 (1997)). Furthermore, these animals show reduced monocyte infiltration into granulomatous lesions induced by the injection of schistosomal or mycobacterial antigens (Boring et al. *J. Clin. Invest.*, 100, 2552-2561 (1997); Warmington et al. *Am J. Path.*, 154, 1407-1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases.

Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1 −/− or CCR2 −/−mice backcrossed to APO-E −/−, LDL-R −/− or Apo B transgenic mice maintained on high fat diets (Boring et al. *Nature*, 394, 894-897 (1998); Gosling et al. *J. Clin. Invest.*, 103, 773-778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is further directed to compounds of Formula I:

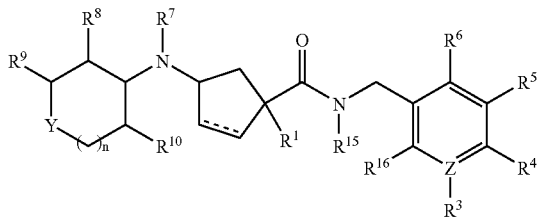

(wherein n, $R^1$, $R^3$, $R^4$, $R^5$, $R^6$, $R^7$, $R^8$, $R^9$, $R^{10}$, $R^{15}$, $R^{16}$ Y and Z are as defined herein) which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of Formula I:

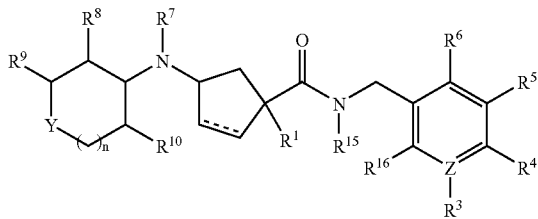

wherein:
Y is selected from: —O—, —$NR^{12}$—, —S—, —SO—, —$SO_2$—, and —$CR^{12}R^{12}$—, —$NSO_2R^{14}$—, —$NCOR^{13}$—, —$CR^{12}COR^{11}$—, —$CR^{12}OCOR^{13}$— and —CO—;
Z is C or N;
$R^1$ is selected from:
 (a) —$SO_2R^{14}$,
 (b) —$C_{0-3}$alkyl-S(O)—$R^{14}$,
 (c) —$C_{1-6}$alkyl-$NR^{12}R^{12}$,
 (d) —$N(CH_3)$—$COR^{13}$,
 (e) —$N(CH_3)$—$SO_2R^{14}$, and
 (f) —$SO_2NR^{12}R^{12}$;
$R^2$ is selected from:
 (a) hydrogen,
 (b) hydroxy,
 (c) halo,
 (d) $C_{1-3}$alkyl unsubstituted or substituted with 1-6 substituents independently selected from fluoro and hydroxy,
 (e) —$NR^{12}R^{12}$,
 (f) —$COR^{11}$,
 (g) —$CONR^{12}R^{12}$,
 (h) —$NR^{12}COR^{13}$,
 (i) —$OCONR^{12}R^{12}$,
 (j) —$NR^{12}CONR^{12}R^{12}$,
 (k) -heterocycle,
 (l) —CN,
 (m) —$NR^{12}$—$SO_2$—$NR^{12}R^{12}$,
 (n) —$NR^{12}$—$SO_2$—$R^{12}$,
 (o) —$SO_2$—$NR^{12}R^{12}$, and
 (p) =O, where $R^2$ is connected to the ring via a double bond;
$R^3$ is selected from:
 (a) hydrogen,
 (b) $C_{1-3}$alkyl unsubstituted or substituted with 1-3 fluoro,
 (c) —O—$C_{1-3}$alkyl unsubstituted or substituted with 1-3 fluoro,
 (d) hydroxy,
 (e) chloro,
 (f) fluoro,
 (g) bromo,
 (h) phenyl,
 (i) heterocycle,
 (j) O, when Z is N, and
 (k) nothing, when Z is N;
$R^4$ is selected from:
 (a) hydrogen,
 (b) $C_{1-3}$alkyl unsubstituted or substituted with 1-3 fluoro,
 (c) —O—$C_{1-3}$alkyl unsubstituted or substituted with 1-3 fluoro,
 (d) hydroxy,
 (e) chloro,
 (f) fluoro,
 (g) bromo,
 (h) phenyl, and
 (i) heterocycle;
$R^5$ is selected from:
 (a) $C_{1-6}$alkyl, unsubstituted or substituted with 1-6 fluoro, hydroxyl, or both,
 (b) —O—$C_{1-6}$alkyl, unsubstituted or substituted with 1-6 fluoro,
 (c) —CO—$C_{1-6}$alkyl, unsubstituted or substituted with 1-6 fluoro,
 (d) —S—$C_{1-6}$alkyl, unsubstituted or substituted with 1-6 fluoro,
 (e) -pyridyl, unsubstituted or substituted with one or more substituents independently selected from: halo, trifluoromethyl, $C_{1-4}$alkyl, and $COR^{11}$,
 (f) fluoro,
 (g) chloro,
 (h) bromo,
 (i) —$C_{4-6}$cycloalkyl,
 (j) —O—$C_{4-6}$cycloalkyl,
 (k) phenyl, unsubstituted or substituted with one or more substituents independently selected from: halo, trifluoromethyl, $C_{1-4}$alkyl, and $COR^{11}$,
 (l) —O-phenyl, unsubstituted or substituted with one or more substituents independently selected from: halo, trifluoromethyl, $C_{1-4}$alkyl, and $COR^{11}$,
 (m) —$C_{3-6}$cycloalkyl, unsubstituted or substituted with 1-6 fluoro,
 (n) —O—$C_{3-6}$cycloalkyl, unsubstituted or substituted with 1-6 fluoro,
 (o) -heterocycle,
 (p) —CN, and
 (q) —$COR^{11}$;
$R^6$ is selected from:
 (a) hydrogen,
 (b) $C_{1-3}$alkyl, unsubstituted or substituted with 1-3 fluoro, (c) —O—$C_{1-3}$alkyl, unsubstituted or substituted with 1-3 fluoro,
(d) hydroxy,
(e) chloro,
(f) fluoro,
(g) bromo,
(h) phenyl, and
(i) heterocycle;

$R^7$ is selected from: hydrogen and $C_{1-6}$alkyl unsubstituted or substituted with 1-3 substituents independently selected from: halo, hydroxy, —$CO_2H$, —$CO_2C_{1-6}$alkyl, and —O—$C_{1-3}$alkyl;

$R^8$ is selected from:
(a) hydrogen,
(b) $C_{1-6}$alkyl, unsubstituted or substituted with 1-6 substituents independently selected from: fluoro, $C_{1-3}$alkoxy, hydroxy, and —$COR^{11}$,
(c) fluoro,
(d) —O—$C_{1-3}$alkyl, unsubstituted or substituted with 1-3 fluoro,
(e) $C_{3-6}$ cycloalkyl,
(f) —O—$C_{3-6}$cycloalkyl,
(g) hydroxy,
(h) —COR11, and
(i) —$OCOR^{13}$,
or $R^7$ and $R^8$ together are $C_{2-4}$alkyl or $C_{0-2}$alkyl-O—$C_{1-3}$alkyl, forming a 5-7 membered ring;

$R^9$ is selected from:
(a) hydrogen,
(b) $C_{1-6}$alkyl, unsubstituted or substituted with 1-6 substituents independently selected from: fluoro, $C_{1-3}$alkoxy, hydroxy, —$COR^{11}$,
(c) $COR^{11}$,
(d) hydroxy, and
(e) —O—$C_{1-6}$alkyl, unsubstituted or substituted with 1-6 substituents independently selected from: fluoro, $C_{1-3}$alkoxy, hydroxy, —$COR^{11}$,
or $R^8$ and $R^9$ together are $C_{1-4}$alkyl or $C_{0-3}$alkyl-O—$C_{0-3}$alkyl, forming a 3-6 membered ring;

$R^{10}$ is selected from:
(a) hydrogen, and
(b) $C_{1-6}$alkyl, unsubstituted or substituted with 1-6 fluoro,
(c) fluoro,
(d) —O—$C_{3-6}$cycloalkyl, and
(e) —O—$C_{1-3}$alkyl, unsubstituted or substituted with 1-6 fluoro,
or $R^8$ and $R^{10}$ together are $C_{2-3}$alkyl, forming 5-6 membered ring, where said $C_{2-3}$alkyl is unsubstituted or substituted with 1-3 substituents independently selected from: halo, hydroxy, —$COR^{11}$, $C_{1-3}$alkyl, and $C_{1-3}$alkoxy,
or $R^8$ and $R^{10}$ together are $C_{1-2}$alkyl-O—$C_{1-2}$alkyl, forming a 6-8 membered ring, where said $C_{1-2}$alkyl-O—$C_{1-2}$alkyl is unsubstituted or substituted with 1-3 substituents independently selected from: halo, hydroxy, —$COR^{11}$, $C_{1-3}$alkyl, and $C_{1-3}$alkoxy,
or $R^8$ and $R^{10}$ together are —O—$C_{1-2}$alkyl-O—, forming a 6-7 membered ring, where said —O—$C_{1-2}$alkyl-O— is unsubstituted or substituted with 1-3 substituents independently selected from: halo, hydroxy, —$COR^{11}$, $C_{1-3}$alkyl, and $C_{1-3}$alkoxy;

$R^{11}$ is independently selected from: hydroxy, hydrogen, $C_{1-6}$ alkyl, —O—$C_{1-6}$alkyl, benzyl, phenyl, and $C_{3-6}$ cycloalkyl, where said alkyl, phenyl, benzyl, and cycloalkyl are unsubstituted or substituted with 1-3 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{12}$ is independently selected from: hydrogen, $C_{1-6}$ alkyl, benzyl, phenyl, $C_{3-6}$ cycloalkyl, where said alkyl, phenyl, benzyl, and cycloalkyl are unsubstituted or substituted with 1-3 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{13}$ is independently selected from: hydrogen, $C_{1-6}$ alkyl, —O—$C_{1-6}$alkyl, benzyl, phenyl and $C_{3-6}$ cycloalkyl, where said alkyl, phenyl, benzyl, and cycloalkyl are unsubstituted or substituted with 1-3 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{14}$ is independently selected from: hydroxy, $C_{1-6}$ alkyl, —O—$C_{1-6}$alkyl, benzyl, phenyl and $C_{3-6}$ cycloalkyl, where said alkyl, phenyl, benzyl, and cycloalkyl groups are unsubstituted or substituted with 1-3 substituents independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^{15}$ and $R^{16}$ are each H, or $R^{15}$ and $R^{16}$ together are —$CH_2CH(R^2)$—, forming a fused ring;

n is 0, 1 or 2;

a dashed line represents an optional single bond;

and pharmaceutically acceptable salts thereof and individual diastereomers thereof.

Compounds of the present invention also include compounds of Formula Ia:

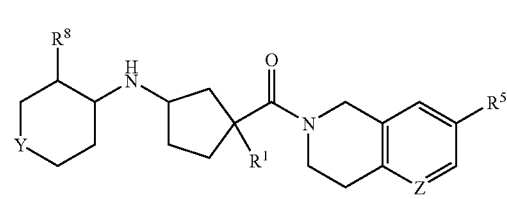

Ia wherein $R^1$, $R^5$, $R^8$, Z, and Y are described herein, and pharmaceutically acceptable salts and individual diastereomers thereof.

Further compounds of the present invention include compounds of formula Ib:

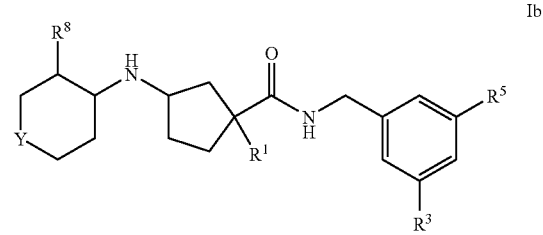

Ib wherein $R^1$, $R^3$, $R^5$, $R^8$, and Y are described herein, and pharmaceutically acceptable salts and individual diastereomers thereof.

Still further compounds of the present invention include compounds of formula Ic:

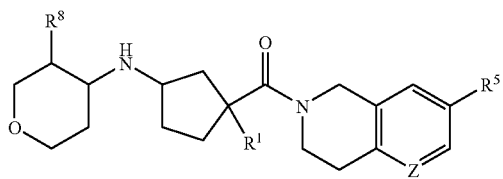

Ic wherein $R^1$, $R^5$, $R^8$, and Z are described herein, and pharmaceutically acceptable salts and individual diastereomers thereof.

Additional compounds of the present invention include compounds of formula Id:

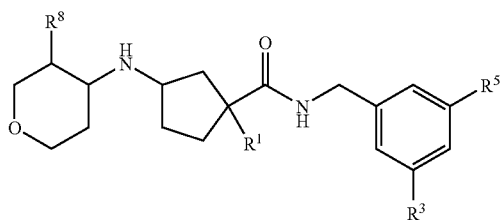

Id wherein $R^1$, $R^3$, $R^5$, and $R^8$ are described herein, and pharmaceutically acceptable salts and individual diastereomers thereof.

Embodiments of the invention also include those wherein Z is N. In certain embodiments when Z is C, $R^3$ is hydrogen, fluoro or trifluoromethyl, and when Z is N, $R^3$ is nothing.

Embodiments of the invention also include those wherein Y is —$CH_2$— or —O—, or wherein Y is O.

In certain embodiments $R^1$ is selected from —$SO_2CH_3$, —$SO_2NH_2$, —$SOCH_3$, and —$SO_2NHCH_3$, and in particular wherein $R^1$ is —$SO_2CH_3$.

In certain embodiments of the present invention one or more of $R^2$, $R^4$, $R^6$, $R^7$, $R^9$ and/or $R^{10}$ are hydrogen.

Embodiments of the invention also include those wherein $R^5$ is selected from $C_{1-6}$alkyl substituted with 1-6 fluoro, —O—$C_{1-6}$alkyl substituted with 1-6 fluoro, chloro, bromo and phenyl, and in particular trifluoromethyl, trifluoromethoxy, chloro, bromo and phenyl.

In certain embodiments of the present invention $R^8$ is selected from hydrogen, $C_{1-3}$alkyl which is unsubstituted or substituted with 1-6 fluoro, —O—$C_{1-3}$alkyl, fluoro and hydroxyl, and in particular hydrogen, trifluoromethyl, methyl, methoxy, ethoxy, ethyl, fluoro and hydroxy.

Embodiments of the invention also include those wherein n is 1.

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo.

As used herein, "alkyl" is intended to mean linear, branched and cyclic carbon structures having no double or triple bonds. $C_{1-8}$, as in $C_{1-8}$alkyl, is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. More broadly, $C_{a-b}$alkyl (where a and b represent whole numbers) is defined to identify the group as having a through b carbons in a linear or branched arrangement. $C_0$, as in $C_0$alkyl is defined to identify the presence of a direct covalent bond. "Cycloalkyl" is an alkyl, part or all of which which forms a ring of three or more atoms.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The term "ring" is employed herein to refer to the formation or existence of a cyclic structure of any type, including free standing rings, fused rings, and bridges formed on existing rings. Rings may be non-aromatic or aromatic. Moreover, the existence or formation of a ring structure is at times herein disclosed wherein multiple substituents are defined "together", as in "where $R^9$ and $R^{10}$ together are $C_{1-2}$alkyl-O—$C_{1-2}$alkyl". In this case a ring is necessarily formed regardless of whether the term "ring" is employed.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media such as ether, ethyl acetate, ethanol, isopropanol, or acetonitrile are employed. Suitable salts are found, e.g. in Remington's Pharmaceutical Sciences, 17th ed., Mack Publishing Company, Easton, Pa., 1985, p. 1418.

Specific compounds within the present invention include a compound which selected from the group consisting of those compounds described in the Examples, and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, in particular CCR-2.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851-856 (1993) which may be readily adapted for measurement of CCR-2 binding.

Receptor affinity in a CCR-2 binding assay was determined by measuring inhibition of $^{125}$I-MCP-1 to the endogenous CCR-2 receptor on various cell types including monocytes, THP-1 cells, or after heterologous expression of the cloned receptor in eukaryotic cells. The cells were suspended in binding buffer (50 mM HEPES, pH 7.2, 5 mM $MgCl_2$, 1 mM $CaCl_2$, and 0.50% BSA or 0.5% human serum) and added to test compound or DMSO and $^{125}$I-MCP-1 at room temperature for 1 h to allow binding. The cells were then collected on GFB filters, washed with 25 mM HEPES buffer containing 500 mM NaCl and cell bound $^{125}$I-MCP-1 was quantified.

In a chemotaxis assay chemotaxis was performed using T cell depleted PBMC (monocytes) isolated from venous whole or leukophoresed blood and purified by Ficoll-Hypaque centrifugation followed by rosetting with neuraminidase-treated sheep erythrocytes. Once isolated, the cells were washed with HBSS containing 0.1 mg/ml BSA and suspended at $1 \times 10^7$ cells/ml. Cells were fluorescently labeled in the dark with 2 µM Calcien-AM (Molecular Probes), for 30 min at 37° C. Labeled cells were washed twice and suspended at $5 \times 10^6$ cells/ml in RPMI 1640 with L-glutamine (without phenol red) containing 0.1 mg/ml BSA. MCP-1 (Peprotech) at 10 ng/ml diluted in same medium or medium alone were added to the bottom wells (27 µl). Monocytes (150,000 cells) were added to the topside of the filter (30 µl) following a 15 min preincubation with DMSO or with various concentrations of test compound. An equal concentration of test compound or DMSO was added to the bottom well to prevent dilution by diffusion. Following a 60 min incubation at 37° C., 5% $CO_2$, the filter was removed and the topside was washed with HBSS containing 0.1 mg/ml BSA to remove cells that had not migrated into the filter. Spontaneous migration (chemokinesis) was determined in the absence of chemoattractant.

In particular, the compounds of the following examples had activity in binding to the CCR-2 receptor in the aforementioned assays, generally with an $IC_{50}$ of less than about 1 µM. Such a result is indicative of the intrinsic activity of the compounds in use as modulators of chemokine receptor activity.

Mammalian chemokine receptors provide a target for interfering with or promoting eosinophil and/or leukocyte function in a mammal, such as a human. Compounds which inhibit or promote chemokine receptor function, are particularly useful for modulating eosinophil and/or leukocyte function for therapeutic purposes. Accordingly, compounds which inhibit or promote chemokine receptor function would be useful in treating, preventing, ameliorating, controlling or reducing the risk of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, endocytosis, exocytosis (e.g., of enzymes, histamine) or inflammatory mediator release, is inhibited.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the compounds of the present invention. In a certain embodiment, the disease or condition is one in which the actions of leukocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); neuropathic pain; systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Inhibitors of chemokine receptor function may also be useful in the treatment and prevention of stroke (Hughes et al., *Journal of Cerebral Blood Flow & Metabolism,* 22:308-317, 2002; Takami et al., *Journal of Cerebral Blood Flow & Metabolism,* 22:780-784, 2002) obesity, type II diabetes, and neuropathic and inflammatory pain. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with modulators of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms), (Trichuriasis, Enterobiasis, Ascariasis, Hookworm, Strongyloidiasis, Trichinosis, filariasis), trematodes (flukes) (Schistosomiasis, Clonorchiasis), cestodes (tape worms) (Echinococcosis, Taeniasis saginata, Cysticercosis), visceral worms, visceral larva migraines (e.g., Toxocara), eosinophilic gastroenteritis (e.g., *Anisaki* sp., *Phocanema* sp.), and cutaneous larva migraines (Ancylostona braziliense, Ancylostoma caninum).

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

The compounds of the present invention are accordingly useful in treating, preventing, ameliorating, controlling or reducing the risk of a wide variety of inflammatory and immunoregulatory disorders and diseases, allergic conditions, atopic conditions, as well as autoimmune pathologies. In a specific embodiment, the present invention is directed to the use of the subject compounds for treating, preventing, ameliorating, controlling or reducing the risk of autoimmune diseases, such as rheumatoid arthritis or psoriatic arthritis.

In another aspect, the instant invention may be used to evaluate putative specific agonists or antagonists of chemokine receptors, including CCR-2. Accordingly, the present invention is directed to the use of these compounds in the preparation and execution of screening assays for compounds that modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-2. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of the present compounds in treating, preventing, ameliorating, controlling or reducing the risk of infection by a retrovirus, in particular, herpes virus or the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a further aspect of the present invention, a subject compound may be used in a method of inhibiting the binding of a chemokine to a chemokine receptor, such as CCR-2, of a target cell, which comprises contacting the target cell with an amount of the compound which is effective at inhibiting the binding of the chemokine to the chemokine receptor.

The subject treated in the methods above is a mammal, for instance a human being, male or female, in whom modulation of chemokine receptor activity is desired. "Modulation" as used herein is intended to encompass antagonism, agonism, partial antagonism, inverse agonism and/or partial agonism. In an aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

As used herein, the term "treatment" refers both to the treatment and to the prevention or prophylactic therapy of the aforementioned conditions.

Combined therapy to modulate chemokine receptor activity for thereby treating, preventing, ameliorating, controlling or reducing the risk of inflammatory and immunoregulatory disorders and diseases, including asthma and allergic diseases, as well as autoimmune pathologies such as rheumatoid arthritis and atherosclerosis, and those pathologies noted above is illustrated by the combination CCR-2 antagonists, such as the compounds of this invention, and other compounds which are known for such utilities.

For example, in treating, preventing, ameliorating, controlling or reducing the risk of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, embrel, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with CCR-2 antagonists, such as the CCR-2 antagonists compounds of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3, CXCR-3 and CCR-5; (j) cholesterol lowering agents such as HMG-CoA reductase inhibitors (lovastatin, simvastatin and pravastatin, fluvastatin, atorvastatin, rosuvastatin, and other statins), sequestrants (cholestyramine and colestipol), cholesterol absorption inhibitors (ezetimibe), nicotinic acid, fenofibric acid derivatives (gemfibrozil, clofibrat, fenofibrate and benzafibrate), and probucol; (k) antidiabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) preparations of glatiramer acetate; (n) preparations of CTLA4Ig; (o) preparations of hydroxychloroquine; (p) Copaxone®; (q) inhibitors of p38; (r) TNF inhibitors and sequestrants; and (s) other compounds such as 5-aminosalicylic acid and prodrugs thereof, antimetabolites such as azathioprine, 6-mercaptopurine and methotrexate, and cytotoxic cancer chemotherapeutic agents.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In treating, preventing, ameliorating, controlling or reducing the risk of conditions which require chemokine receptor modulation an appropriate dosage level will generally be about 0.001 to 500 mg per kg patient body weight per day which can be administered in single or multiple doses. In certain embodiments the dosage level will be about 0.001 to about 400 mg/kg per day; or from about 0.01 to about 300 mg/kg per day; or from about 0.1 to about 250 mg/kg per day, or from about 0.5 to about 100 mg/kg per day. A suitable dosage level may be about 0.001 to 400 mg/kg per day, about 0.01 to 250 mg/kg per day, about 0.05 to 100 mg/kg per day, or about 0.1 to 50 mg/kg per day. Within this range the dosage may be 0.005 to 0.05, 0.05 to 0.5, 0.5 to 5 or 5 to 50 mg/kg per day. For oral administration, the compositions may be provided in the form of tablets containing 0.1 to 1000 milligrams of the active ingredient, or 1.0 to 500, or 2.0 to 500, or 3.0 to 200, particularly 0.1, 1, 5, 10, 15, 20, 25, 30, 50, 75, 100, 125, 150, 175, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, or once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

SCHEMES

Several methods for preparing the compounds of this invention are illustrated in the following Schemes and Examples. Starting materials are made by known procedures or as illustrated.

One of the principal routes used for preparation of compounds (I) within the scope of the instant invention which bear a 1,1,3-trisubstituted cyclopentane framework is detailed in Schemes 1A-1D.

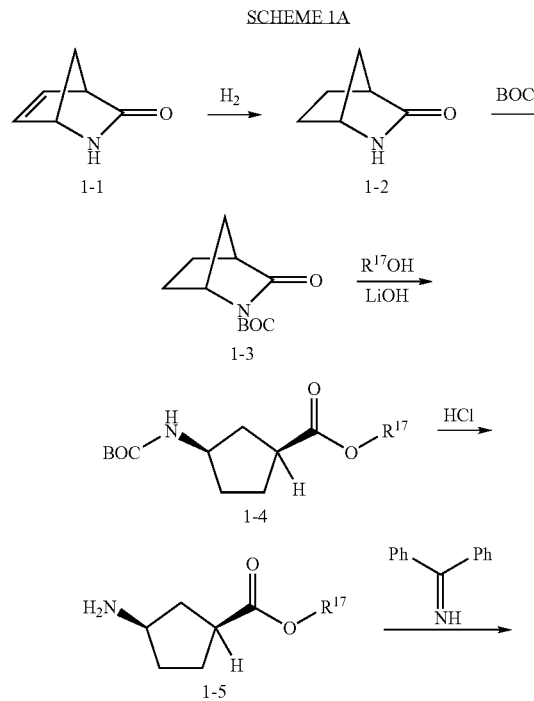

-continued

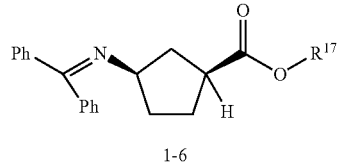

1-6

According to this, the commercially available homochiral lactam 1-1 is hydrogenated and the saturated 1-2 is treated with $BOC_2O$ in the presence of a suitable catalyst, e.g. N,N-dimethylamino pyridine. A base catalyzed cleavage of the amide bond in the presence of a suitable alcohol $R^{17}$—OH provides then the respective ester 1-4. The BOC-protecting group is removed, preferably with an acid such as HCl in a aprotic solvent, such as dioxane, to yield the amine 1-5 in a form of a salt. When this amine is mixed with benzophenone imine, the respective Schiff base 1-6 is formed, which can be obtained in pure form by simple filtration to remove ammonium chloride.

The enolate formed from ester 1-6 with a strong base, such as LDA can be reacted with alkyl disulfides $R^{16}$—S—S—$R^{16}$, intermediate 1-7 shown in Scheme 2B. These reactions produce a mixture of the respective cis-(1-7a) and trans-(1-7b—not shown) diastereoisomers, which can be separated by a suitable chromatography. In most cases, normal phase flash chromatography on deactivated silica gel can be applied with success.

SCHEME 1B

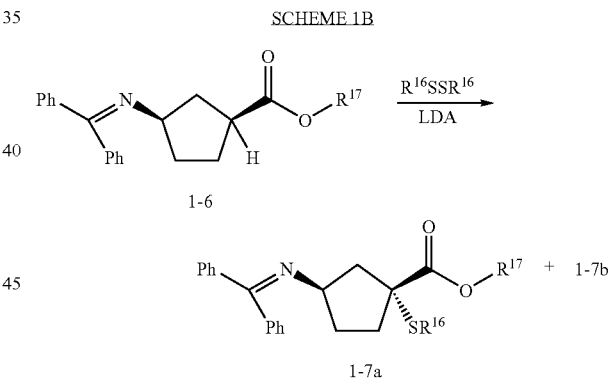

The desired cis diastereoisomers 1-7a and 1-8a are then treated with an acid such as HCl to aid hydrolysis of the imine group and the resulting amino group is suitably protected e.g. in a form of a tert-butoxycarbonyl amide (Scheme 1C). The ester group present in intermediates 1-10a is then cleaved. The applied procedure depends on the nature of the ester: e.g. a benzyl ester can be cleaved by hydrogenolysis, an tert-Butyl ester under aprotic acidic conditions and a alkyl ester can be hydrolyzed under either acidic or basic conditions. The formed acids are then coupled with suitable amines ($R^{19}R^{18}NH$) using a suitable coupling agent such as EDC or PyBrop in DCM. The BOC protecting group is then removed with an acid. A reductive alkylation of amines 1-13a with suitable tetrahydropyran ketones gives the intermediate sulfide which can be oxidized to the sulfone (I) or sulfoxide chemokine modulators using a suitable oxidizing reagent.

SCHEME 1C

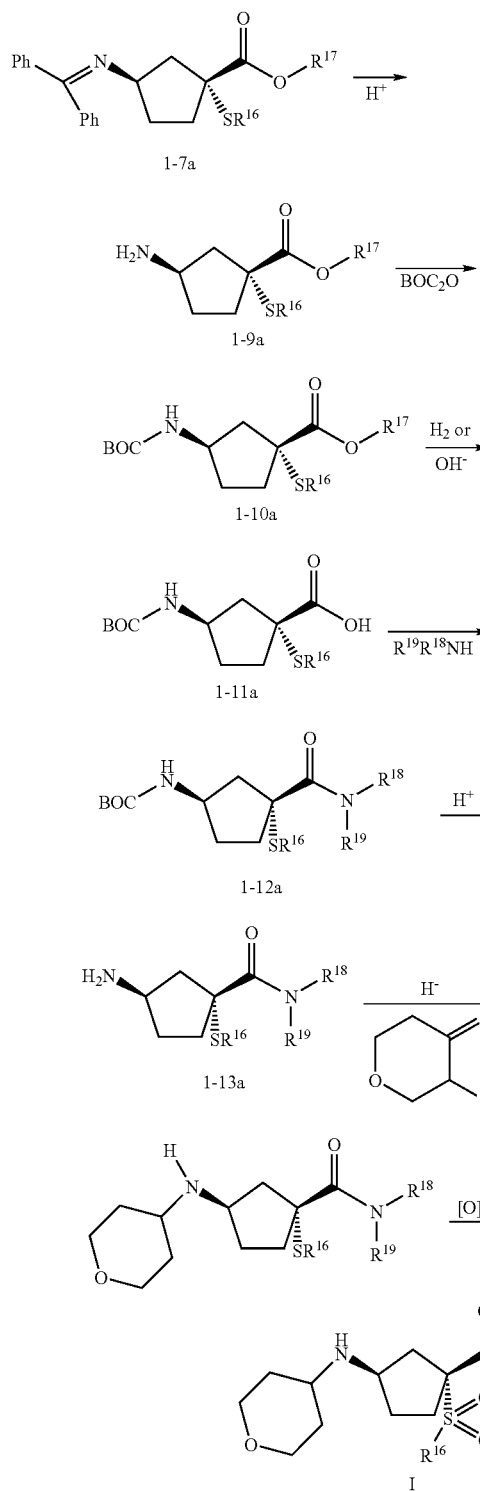

As an alternate route, Intermediates 1-12a can be transformed into the sulfoxides 1-15a or sulfones 1-14a directly as shown in Scheme 1D. Removal of the BOC protecting group and reductive alkylation of the resulting amine with a tetrahydropyranone would give chemokine modulators (I).

SCHEME 1D

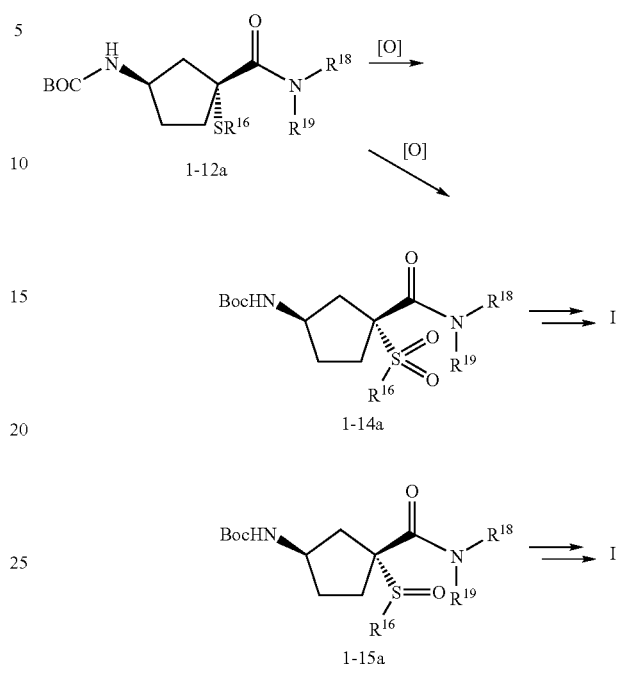

In some cases the order of carrying out the foregoing reaction schemes may be varied to facilitate the reaction or to avoid unwanted reaction products.

The following are representative procedures for the preparation of the compounds used in the following Examples or which can be substituted for the compounds used in the following Examples which may not be commercially available.

EXAMPLES

Intermediate 1

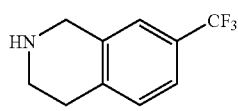

Step A

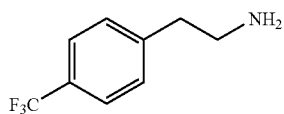

To a solution of 4-trifluoromethyl phenylacetonitrile (40 g, 220 mmol) in 2N $NH_3$/MeOH (400 mL) was added Raney Ni (~4.0 g). The reaction mixture was placed in a par-shaker and shook under 50 lb pressure overnight. The solution was filtered through celite and concentrated in vacuo to yield the desired amine (38 g, 95%). ESI-MS calc. For $C_9H_{10}F_3N$: 189. Found: 190 (M+H).

Step B

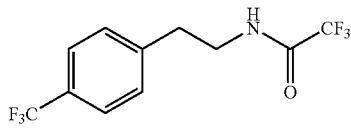

The above amine (Step A, Intermediate 1) (38 g, 200 mmol) and DEA (52 mL, 300 mmol) were dissolved in DCM (300 mL). The solution was cooled to 0° C. before TFAA (36 mL, 250 mmol) was added slowly. The reaction mixture was stirred in the ice bath for another 10 minutes before warmed up to room temperature. The reaction was completed in 30 minutes and dumped in water and extracted with DCM (2×). The organic layer was washed with 1N HCl and saturated NaCl solution, dried over $MgSO_4$, and concentrated in vacuo to yield the desired amide (56 g, 98%). ESI-MS calc. For C11H9F6NO: 285. Found: 286 (M+H).

Step C

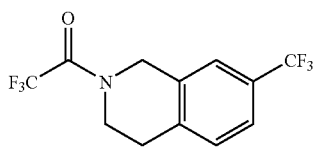

To a mixture of the amide (Step B, Intermediate 1) (73 g, 260 mmol) and paraformialdehyde (11.5 g, 385 mmol) was added 200 mL of acetic acid. The reaction mixture was stirred at room temperature for 5 min before concentrated sulfuric acid (200 mL). An exothermic reaction was observed. After 30 min, TLC showed a complete conversion. The mixture was cooled to RT before poured onto ice water (2000 mL) and extracted with EtOAc (3×500 mL). Combined organic layers were washed with water (2×), saturated $NaHCO_3$, and brine, dried over $MgSO_4$, filtered, evaporated and dried in vacuum. The desired amide (72.7 g, 96%) was obtained as a light-yellow solid. 1H NMR (400 MHz, CDCl3) δ 7.22 (q, J=11.67 Hz, 8.46 Hz, 1H), 7.11 (t, J=10.53 Hz, 1H), 7.03 (d, J=11.67 Hz, 1H), 4.79 (d, J=23.57 Hz, 2H), 3.91 (t, J=6.18Hz, 1H), 3.87 (t, J=5.72 Hz, 1H), 2.97 (m, 2H).
ESI-MS calc. For C12H9F6NO: 297. Found: 298 (M+H).

Step D

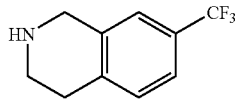

The amide (Step C, Intermediate 1) (50 g, 168 mmol) was dissolved in EtOH (200 mL) before solid $K_2CO_3$ (50 g, 360 mmol) and $H_2O$ (50 mL) were added. The reaction mixture was refluxed for 15 hours before concentrated in vacuo. The concentrate was diluted with $H_2O$ (100 mL) and extracted with DCM (5×). Combined organic layers were dried over $MgSO_4$, filtered, concentrated and purified on FC (10% [aq. NH4OH/MeOH 1/9]/DCM) to yield the amine (Step D, Intermediate 1) (30 g, 89%). 1H NMR (400 MHz, CDCl3) δ 7.11 (d, J=8.4 Hz, 1H), 7.01 (bd, J=8.4 Hz, 1H), 6.89 (s, 1H), 4.03 (s, 2H), 3.15 (t, J=6.1 Hz, 2H), 2.80 (t, J=5.6 Hz, 2H), 1.80 (s, 1H). ESI-MS calc. For C10H10F3N: 201. Found: 202 (M+H).

Intermediate 2

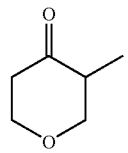

Intermediate 2 was prepared according to the procedure described in *J. Am. Chem. Soc.*, 1991, 113, 2079-2089.

Example 1

Step A

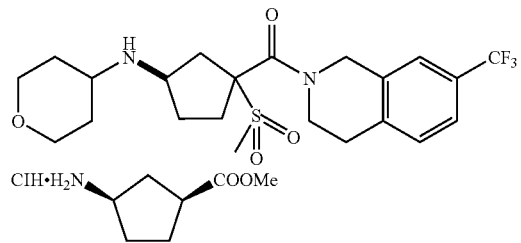

A mixture of (1S)-(+)-2-azabicyclo[2.2.1]hept-5-en-3-one (10.3 g, 94.4 mmol) in EtOAc (200 mL) and 10% Pd/C (0.5 gm), was hydrogenated at room temperature under a hydrogen balloon. After 24 h the reaction mixture was filtered and evaporated leaving behind 10.4 g (100%) of a product that was taken in 250 mL methanol and HCl (12M, 6 mL). The resultant mixture was stirred at RT, until the reaction was complete (72 h). Evaporation of methanol followed by drying under high vacuum, yielded the title compound as an off white solid (16.0 g, 96%).
$^1$H NMR ($D_2O$, 500 MHz): 3.70 (s, 3H), 3.01 (m, 1H), 2.38 (m, 1H), 2.16-1.73 (m, 6H).

Step B

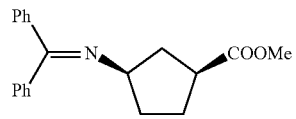

To a suspension of the intermediate from Step A (10.2 g, 56.8 mmol) in dry dichloromethane (200 mL) was added benzophenone imine (10.2 g, 56.8 mmol) at room temperature and the resultant mixture was stirred for 24 h. The reaction mixture was filtered and the filtrate was evaporated, to leave behind a yellow oil that was triturated with ether (100 mL), filtered and evaporated. This operation was repeated twice to ensure that the product was free of ammonium chloride impurities. The resultant oil was thoroughly dried under vacuum to yield the title compound (18.03 g, >100%) and required no further purification. $^1$H NMR (CDCl$_3$, 500 MHz): 7.5-7.18 (m, 10H), 3.75 (m, 1H), 3.7 (s, 3H), 2.78 (m, 1H), 2.26-1.71 (m, 6H).

Step C

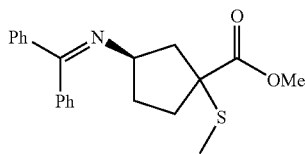

To a flame-dried 500 mL round-bottomed flask, was added dry THF (50 mL). The solution was cooled to −78° C. before iPr₂N (2.63 mL, 18.8 mmol), 2.5 M nBuLi (7.5 mL, 18.8 mmol), and a solution of the Schiff base (Step B) (5 g, 16.3 mmol) in THF (20 mL), were added sequentially. The reaction mixture was stirred at −78° C. for 30 minutes before methyl disulfide (4.4 mL, 49 mmol) was added. After the reaction was stirred for another hour, the mixture was quenched with saturated NH₄Cl, extracted with ether, dried over MgSO4, and concentrated. The crude product was purified by MPLC (10/90 EtOAc/Hexanes) to yield the title compound (3.98 g, 69.0%). LC-MS for $C_{21}H_{24}NO_2S$ [M⁺H⁺] calculated 354.14. Found 354.25.

Step D

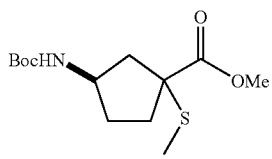

The alkylated Schiff base (Step C, Example 1) (3.98 g, 11.3 mmol) was dissolved in THF (35 mL) before 2N HCl (35 mL) was added. The reaction mixture was stirred and monitored by TLC. After completion of reaction, the mixture was concentrated in vacuo to remove THF. The aqueous layer was basified to pH 9.0 with saturated Na₂CO₃ solution and extracted with DCM. The organic layer was dried over MgSO₄ and Boc-anhydride (3.3 g, 15 mmol) was added. The reaction was stirred at room temperature overnight before extracted with DCM, dried over MgSO₄, and concentrated in vacuo. The crude product was purified by MPLC (35/65, EtOAc/Hexanes) to yield the title compound (2.10 g, 64.4%). LC-MS for $C_{13}H_{24}NO_4S$ [M⁺H⁺] calculated 290.13. Found 190.1 (-Boc).

Step E

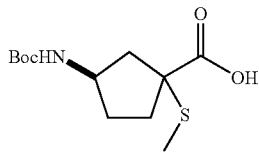

The ester (Step D, Example 1) (2.10 g, 7.27 mmol) was dissolved in MeOH (10 mL) and THF (10 mL) before a solution of LiOH (1.5 g, 36.3 mmol) in H₂O (10 mL) was added. The mixture was heated at 60° C. overnight before concentrated in vacuo to get rid of organic solvents. The aqueous layer was washed with hexanes, acidified to pH 7-4, and extracted with DCM (3×). Combined organic layer was dried over anhydrous MgSO₄ and concentrated to dryness. The crude product was used on next step.

Step F

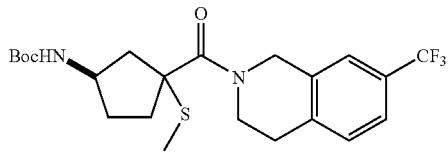

The acid (Step E, Example 1) (500 mg, 1.82 mmol), Intermediate 1 (366 mg, 1.82 mmol), and HOAT (250 mg, 1.82 mmol) were dissolved in DCM (20 mL) before EDC (525 mg, 2.73 mmol) was added. The resulting mixture was stirred overnight before washed with saturated NaHCO₃, H₂O (2×), and brine, dried over MgSO₄, and concentrated in vacuo. The crude product was purified by preparation plate (30/70, EtOAc/Hexanes) to yield the title compound (742 mg, 89.2%). LC-MS for $C_{22}H_{30}F_3N_2O_3S$ [M⁺H⁺] calculated 459.19. Found 403.15 (-tert-butyl group).

Step G

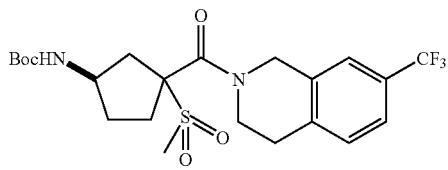

Intermediate (Step F, Example 1) (200 mg, 0.44 mmol) was dissolved in iPrOH (5 mL) before a solution of oxone (540 mg, 0.88 mmol) in H₂O (5 mL) was added. The mixture was stirred at room temperature for 2 hours before concentrated to dryness. The concentrate was diluted with ether, washed with H₂O (3×), dried over anhydrous MgSO₄, and concentrated in vacuo to yield the title compound (212 mg, 99.1%). LC-MS for $C_{22}H_{30}F_3N_2O_5S$ [M⁺H⁺] calculated 491.17. Found 391.15 (-Boc group).

Step H

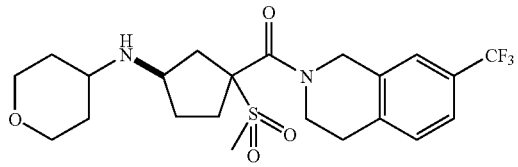

The product from Step G (212 mg) was dissolved in 4 M HCl in dioxane and stirred for 2 hours at room temperature before beign concentrated under reduced pressure to give 183 mg of the desired HCl salt. This salt (100 mg, 0.356 mmol) was combined with DIEA (70 µL, 0.384 mmol), tetrahydro-4H-pyran-4-one (52 µL, 0.513 mmol), 4 Å molecular sieves, and sodium triacetoxyborohydride (270 mg, 1.28 mmol) in DCM. The resulting reaction mixture was stirred for several days before being washed with saturated aqeous sodium bicarbonate (×3). The combined aqeous layers were back-extracted with DCM (×4) and the combined organic layers were dried over Na₂SO₄, filtered, and concentrated under reduced pressure. The two isomers were resolved on the preparation plates (4/95.6/0.4, MeOH/DCM/NH$_4$OH). LC-MS for C$_{22}$H$_{30}$F$_3$N$_2$O$_4$S [M+H$^+$] calculated 475.18. Found 475.15.

Example 2

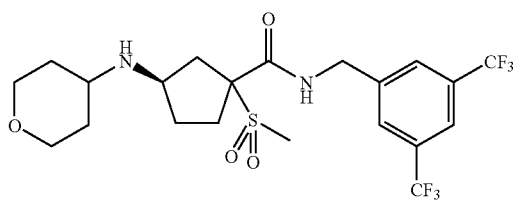

Step A

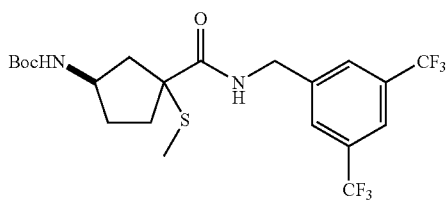

The above amide was prepared in a procedure analogous to that described in Example 1, Step F, except that Intermediate 1 was replaced with 3,5-bis(trifluoromethyl) benzylamine. LC-MS for C$_{21}$H$_{27}$N$_2$O$_3$S [M+H$^+$] calculated 501.16. Found 445.15 (loss of the t-butyl group).

Step B

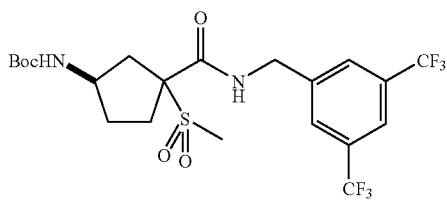

The sulfide, preparation of which was described in Example 1, Step A (200 mg, 0.4 mmol) was dissolved in isopropanol (7 mL) before a solution of oxone (500 mg, 0.8 mmol) in H$_2$O (7 mL) was added. The mixture was stirred at room temperature for 2 h before being concentrated to dryness. The concentrate was diluted with ether, washed with H$_2$O (3×), dried over anhydrous MgSO$_4$, and concentrated in vacuo to yield 207 mg (97%) of the desired compound. LC-MS for C$_{21}$H$_{27}$F$_6$N$_2$O$_5$S [M+H$^+$] calculated 533.15. Found 433.15 (-BOC-group).

Step C

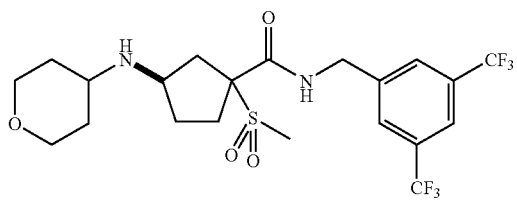

This compound was prepared starting from the previously described sulfone using the procedures detailed in Example 1, Step H, using the product from the previous step. The cis- and trans-isomers were separated by preparative TLC with the less polar compound being the cis isomer. LC-MS for C$_{21}$H$_{27}$F$_6$N$_2$O$_4$S [M+H$^+$] calculated 517.15. Found 517.15.

Example 3

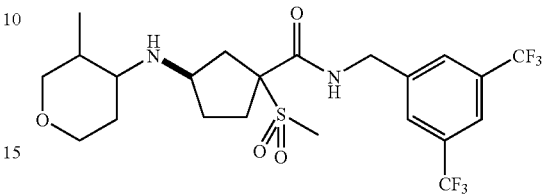

This compound was prepared as detailed in Example 2 using Intermediate 2 instead of tetrahydro-4H-pyran-4-one. The two pairs of isomers were separated by preparative TLC (MeOH:DCM:NH$_4$OH/3:96.7:0.3). LC-MS for C$_{22}$H$_{29}$F$_6$N$_2$O$_4$S [M+H$^+$] calculated 531.17. Found 531.25.

Example 4

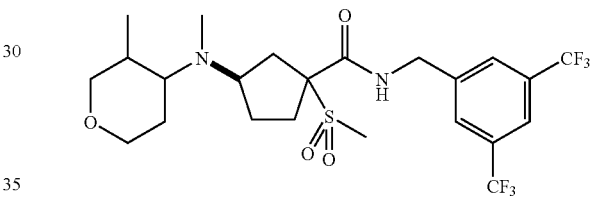

A mixture of the product described in Example 3 (more polar isomer, 30 mg, 0.058 mmol), formaldehyde (37% wt in H$_2$O, 15 µL, 0.17 mmol), TFA, NaCNBH$_3$ (20 mg, 0.29 mmol), and MeOH (5 mL) was stirred at room temperature overnight before being concentrated in vacuo and purified by preparative TLC (MeOH:DCM:NH$_4$OH/4:95.6:0.4) to yield Example 4 (11 mg, 35.7%). LC-MS for C$_{23}$H$_{31}$F$_6$N$_2$O$_4$S [M+H$^-$] calculated 545.18. Found 545.2.

Example 5

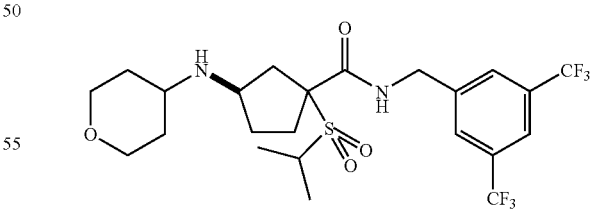

This compound was prepared as detailed in Examples 1 and 2, except that methyl disulfide was replaced with isopropyl disulfide in Example 1, Step C. LC-MS for C$_{23}$H$_{31}$F$_6$N$_2$O$_4$S [M+H]$^+$ calculated 545.18, found 545.2.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I:

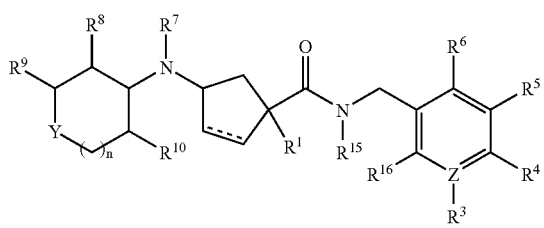

I wherein:

Y is selected from: —O—, —NR$^{12}$—, —S—, —SO—, —SO$_2$—, and —CR$^{12}$R$^{12}$—, —NSO$_2$R$^{14}$—, —NCOR$^{13}$—, —CR$^{12}$COR$^{11}$—, —CR$^{12}$OCOR$^{13}$— and —CO—;

Z is C or N;

R$^1$ is selected from:
(a) —SO$_2$R$^{14}$,
(b) —C$_{0-3}$alkyl-S(O)—R$^{14}$,
(c) —C$_{1-6}$alkyl-NR$^{12}$R$^{12}$,
(d) —N(CH$_3$)—COR$^{13}$,
(e) —N(CH$_3$)—SO$_2$R$^{14}$, and
(f) —SO$_2$NR$^{12}$R$^{12}$;

R$^2$ is selected from:
(a) hydrogen,
(b) hydroxy,
(c) halo,
(d) C$_{1-3}$alkyl unsubstituted or substituted with 1-6 substituents independently selected from fluoro and hydroxy,
(e) —NR$^{12}$R$^{12}$,
(f) —COR$^{11}$,
(g) —CONR$^{12}$R$^{12}$,
(h) —NR$^{12}$COR$^{13}$,
(i) —OCONR$^{12}$R$^{12}$,
(j) —NR$^{12}$CONR$^{12}$R$^{12}$,
(k) -heterocycle,
(l) —CN,
(m) —NR$^{12}$—SO$_2$—NR$^{12}$R$^{12}$,
(n) —NR$^{12}$—SO$_2$—R$^{12}$,
(o) —SO$_2$—NR$^{12}$R$^{12}$, and
(p) =O;

R$^3$ is selected from:
(a) hydrogen,
(b) C$_{1-3}$alkyl unsubstituted or substituted with 1-3 fluoro,
(c) —O—C$_{1-3}$alkyl unsubstituted or substituted with 1-3 fluoro,
(d) hydroxy,
(e) chloro,
(f) fluoro,
(g) bromo,
(h) phenyl,
(i) heterocycle,
(j) O, when Z is N, and
(k) nothing, when Z is N;

R$^4$ is selected from:
(a) hydrogen,
(b) C$_{1-3}$alkyl unsubstituted or substituted with 1-3 fluoro,
(c) —O—C$_{1-3}$alkyl unsubstituted or substituted with 1-3 fluoro,
(d) hydroxy,
(e) chloro,
(f) fluoro,
(g) bromo,
(h) phenyl, and
(i) heterocycle;

R$^5$ is selected from:
(a) C$_{1-6}$alkyl, unsubstituted or substituted with 1-6 fluoro, hydroxyl, or both,
(b) —O—C$_{1-6}$alkyl, unsubstituted or substituted with 1-6 fluoro,
(c) —CO—C$_{1-6}$alkyl, unsubstituted or substituted with 1-6 fluoro,
(d) —S—C$_{1-6}$alkyl, unsubstituted or substituted with 1-6 fluoro,
(e) -pyridyl, unsubstituted or substituted with one or more substituents independently selected from: halo, trifluoromethyl, C$_{1-4}$alkyl, and COR$^{11}$,
(f) fluoro,
(g) chloro,
(h) bromo,
(i) —C$_{4-6}$cycloalkyl,
(j) —O—C$_{4-6}$cycloalkyl,
(k) phenyl, unsubstituted or substituted with one or more substituents independently selected from: halo, trifluoromethyl, C$_{1-4}$alkyl, and COR$^{11}$,
(l) —O-phenyl, unsubstituted or substituted with one or more substituents independently selected from: halo, trifluoromethyl, C$_{1-4}$alkyl, and COR$^{11}$,
(m) —C$_{3-6}$cycloalkyl, unsubstituted or substituted with 1-6 fluoro,
(n) —O—C$_{3-6}$cycloalkyl, unsubstituted or substituted with 1-6 fluoro,
(o) -heterocycle,
(p) —CN, and
(q) —COR$^{11}$;

R$^6$ is selected from:
(a) hydrogen,
(b) C$_{1-3}$alkyl, unsubstituted or substituted with 1-3 fluoro,
(c) —O—C$_{1-3}$alkyl, unsubstituted or substituted with 1-3 fluoro,
(d) hydroxy,
(e) chloro,
(f) fluoro,
(g) bromo,
(h) phenyl, and
(i) heterocycle;

R$^7$ is selected from: hydrogen and C$_{1-6}$alkyl unsubstituted or substituted with 1-3 substituents independently selected from: halo, hydroxy, —CO$_2$H, —CO$_2$ C$_{1-6}$alkyl, and —O—C$_{1-3}$alkyl;

R$^8$ is selected from:
(a) hydrogen,
(b) C$_{1-6}$alkyl, unsubstituted or substituted with 1-6 substituents independently selected from: fluoro, C$_{1-3}$alkoxy, hydroxy, and —COR$^{11}$,
(c) fluoro,
(d) —O—C$_{1-3}$alkyl, unsubstituted or substituted with 1-3 fluoro,
(e) C$_{3-6}$ cycloalkyl,
(f) —O—C$_{3-6}$cycloalkyl,
(g) hydroxy,
(h) —COR$^{11}$, and
(i) —OCOR$^{13}$,
or R$^7$ and R$^8$ together are C$_{2-4}$alkyl or C$_{0-2}$alkyl-O—C$_{1-3}$alkyl, forming a 5-7 membered ring;

R$^9$ is selected from:
(a) hydrogen,
(b) C$_{1-6}$alkyl, unsubstituted or substituted with 1-6 substituents independently selected from: fluoro, C$_{1-3}$alkoxy, hydroxy, —COR$^{11}$,
(c) COR$^{11}$,
(d) hydroxy, and
(e) —O—C$_{1-6}$alkyl, unsubstituted or substituted with 1-6 substituents independently selected from: fluoro, C$_{1-3}$alkoxy, hydroxy, —COR$^{11}$,
or R$^8$ and R$^9$ together are C$_{1-4}$alkyl or C$_{0-3}$alkyl-O—C$_{0-3}$alkyl, forming a 3-6 membered ring;

R$^{10}$ is selected from:
(a) hydrogen,
(b) C$_{1-6}$alkyl, unsubstituted or substituted with 1-6 fluoro,
(c) fluoro,
(d) —O—C$_{3-6}$cycloalkyl, and
(e) —O—C$_{1-3}$alkyl, unsubstituted or substituted with 1-6 fluoro,
or R$^8$ and R$^{10}$ together are C$_{2-3}$alkyl, forming 5-6 membered ring, where said C$_{2-3}$alkyl is unsubstituted or substituted with 1-3 substituents independently selected from: halo, hydroxy, —COR$^{11}$, C$_{1-3}$alkyl, and C$_{1-3}$alkoxy,
or R$^8$ and R$^{10}$ together are C$_{1-2}$alkyl-O—C$_{1-2}$alkyl, forming a 6-8 membered ring, where said C$_{1-2}$alkyl-O—C$_{1-2}$alkyl is unsubstituted or substituted with 1-3 substituents independently selected from: halo, hydroxy, —COR$^{11}$, C$_{1-3}$alkyl, and C$_{1-3}$alkoxy,
or R$^8$ and R$^{10}$ together are —O—C$_{1-2}$alkyl-O—, forming a 6-7 membered ring, where said —O—C$_{1-2}$alkyl-O— is unsubstituted or substituted with 1-3 substituents independently selected from: halo, hydroxy, —COR$^{11}$, C$_{1-3}$alkyl, and C$_{1-3}$alkoxy;

R$^{11}$ is independently selected from: hydroxy, hydrogen, C$_{1-6}$alkyl, —O—C$_{1-6}$alkyl, benzyl, phenyl, and C$_{3-6}$cycloalkyl, where said alkyl, phenyl, benzyl, and cycloalkyl are unsubstituted or substituted with 1-3 substituents independently selected from: halo, hydroxy, C$_{1-3}$alkyl, C$_{1-3}$alkoxy, —CO$_2$H, —CO$_2$—C$_{1-6}$alkyl, and trifluoromethyl;

R$^{12}$ is independently selected from: hydrogen, C$_{1-6}$alkyl, benzyl, phenyl, C$_{3-6}$ cycloalkyl, where said alkyl, phenyl, benzyl, and cycloalkyl are unsubstituted or substituted with 1-3 substituents independently selected from: halo, hydroxy, C$_{1-3}$alkyl, C$_{1-3}$alkoxy, —CO$_2$H, —CO$_2$—C$_{1-6}$ alkyl, and trifluoromethyl;

R$^{13}$ is independently selected from: hydrogen, C$_{1-6}$ alkyl, —O—C$_{1-6}$alkyl, benzyl, phenyl and C$_{3-6}$ cycloalkyl, where said alkyl, phenyl, benzyl, and cycloalkyl are unsubstituted or substituted with 1-3 substituents independently selected from: halo, hydroxy, C$_{1-3}$alkyl, C$_{1-3}$alkoxy, —CO$_2$H, —CO$_2$—C$_{1-6}$ alkyl, and trifluoromethyl;

R$^{14}$ is independently selected from: hydroxy, C$_{1-6}$alkyl, —O—C$_{1-6}$alkyl, benzyl, phenyl and C$_{3-6}$ cycloalkyl, where said alkyl, phenyl, benzyl, and cycloalkyl groups are unsubstituted or substituted with 1-3 substituents independently selected from: halo, hydroxy, C$_{1-3}$alkyl, C$_{1-3}$alkoxy, —CO$_2$H, —CO$_2$—C$_{1-6}$ alkyl, and trifluoromethyl;

R$^{15}$ and R$^{16}$ are each H, or R$^{15}$ and R$^{16}$ together are —CH$_2$CH(R$^2$)—, forming a fused ring;

n is 0, 1 or 2;

a dashed line represents an optional single bond;

or a pharmaceutically acceptable salt thereof or an individual diastereomer thereof.

2. The compound of claim 1 of the Formula Ia:

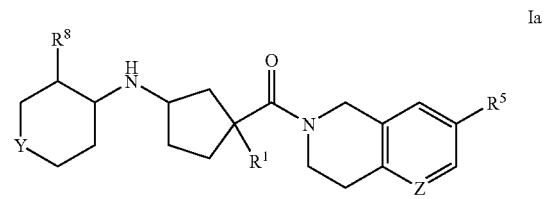

Ia or a pharmaceutically acceptable salt thereof or an individual diastereomer thereof.

3. The compound of claim 1 of the Formula Ib:

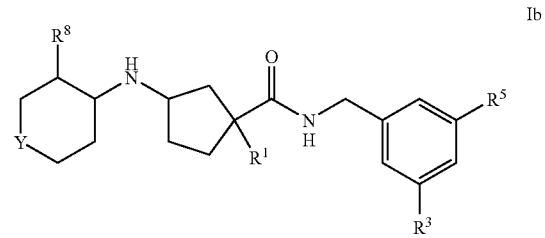

Ib or a pharmaceutically acceptable salt thereof or an individual diastereomer thereof.

4. The compound of claim 1 of the Formula Ic:

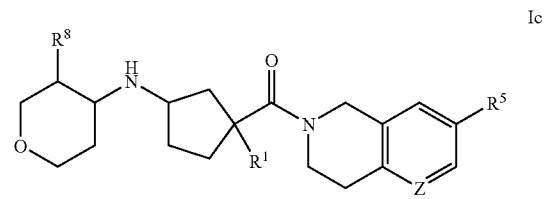

Ic or a pharmaceutically acceptable salt thereof or an individual diastereomer thereof.

5. The compound of claim 1 of the Formula Id:

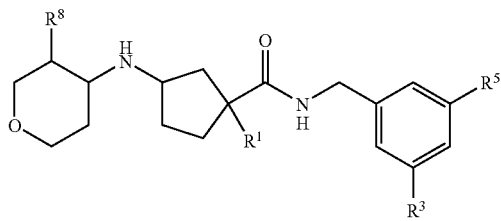

or a pharmaceutically acceptable salt thereof or an individual diastereomer thereof.

6. The compound of claim 1 wherein when Z is C, $R^3$ is hydrogen, fluoro or trifluoromethyl, and when Z is N, $R^3$ is nothing, or a pharmaceutically acceptable salt thereof or an individual diastereomer thereof.

7. The compound of claim 1 wherein Y is $-CH_2-$ or $-O-$, or a pharmaceutically acceptable salt thereof or an individual diastereomer thereof.

8. The compound of claim 1 wherein $R^1$ is selected from $-SO_2CH_3$, $-SO_2NH_2$, $-SOCH_3$, and $-SO_2NHCH_3$, or a pharmaceutically acceptable salt thereof or an individual diastereomer thereof.

9. The compound of claim 1 wherein $R^5$ is selected from $C_{1-6}$alkyl substituted with 1-6 fluoro, $-O-C_{1-6}$alkyl substituted with 1-6 fluoro, chloro, bromo and phenyl, or a pharmaceutically acceptable salt thereof or an individual diastereomer thereof.

10. The compound of claim 1 wherein $R^8$ is selected from hydrogen, $C_{1-3}$alkyl which is unsubstituted or substituted with 1-6 fluoro, $-O-C_{1-3}$alkyl, fluoro and hydroxyl, or a pharmaceutically acceptable salt thereof or an individual diastereomer thereof.

11. A compound selected from:

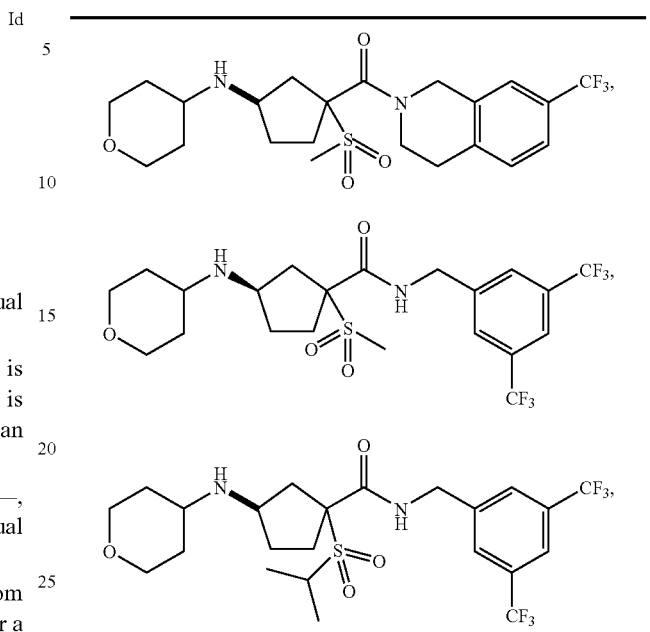

or a pharmaceutically acceptable salt thereof or an individual diastereomer thereof.

12. A pharmaceutical composition which comprises an inert carrier and the compound of claim 1, or a pharmaceutically acceptable salt thereof or an individual diastereomer thereof.

13. A method of treating an inflammatory or immunoregulatory disorder or disease comprising the administration of a therapeutically effective amount of the compound of claim 1 to a patient in need of treatment wherein said disorder or disease is rheumatoid arthritis.

\* \* \* \* \*